United States Patent
Okayama et al.

(10) Patent No.: US 8,382,884 B2
(45) Date of Patent: Feb. 26, 2013

(54) PARTICULATE MATTER DETECTION DEVICE

(75) Inventors: Tatsuya Okayama, Saitama (JP); Masanobu Miki, Saitama (JP); Keizo Iwama, Saitama (JP); Hidetaka Ozawa, Saitama (JP); Makoto Hattori, Saitama (JP); Atsuo Kondo, Aichi (JP); Takeshi Sakuma, Aichi (JP); Takashi Egami, Aichi (JP); Masahiro Tokuda, Aichi (JP)

(73) Assignees: Honda Motor Co., Ltd., Tokyo (JP); NGK Insulators, Ltd., Nagoya, Aichi (JP)

(*) Notice: Subject to any disclaimer, the term of this patent is extended or adjusted under 35 U.S.C. 154(b) by 496 days.

(21) Appl. No.: 12/705,271

(22) Filed: Feb. 12, 2010

(65) Prior Publication Data
US 2010/0206167 A1 Aug. 19, 2010

(30) Foreign Application Priority Data
Feb. 16, 2009 (JP) ................................. 2009-032954

(51) Int. Cl.
*B03C 3/68* (2006.01)

(52) U.S. Cl. .......... 96/19; 60/275; 73/28.02; 73/864.71; 95/3; 96/30; 96/31

(58) Field of Classification Search ................ 96/18, 19, 96/21–24, 30, 31, 69, 99; 95/2, 3, 6, 7; 55/385.3, 55/DIG. 30; 60/275; 73/28.02, 864.71
See application file for complete search history.

(56) References Cited

U.S. PATENT DOCUMENTS

| 4,944,778 | A | * | 7/1990 | Yanagawa | 96/66 |
| 5,055,118 | A | * | 10/1991 | Nagoshi et al. | 96/88 |
| 6,187,271 | B1 | * | 2/2001 | Lee et al. | 422/121 |
| 7,261,767 | B2 | * | 8/2007 | Choi et al. | 96/69 |
| 7,294,176 | B2 | * | 11/2007 | Kim et al. | 96/69 |
| 7,507,275 | B2 | * | 3/2009 | Kim et al. | 96/69 |
| 2004/0226448 | A1 | * | 11/2004 | Griffiths et al. | 96/67 |
| 2006/0227486 | A1 | * | 10/2006 | Kim et al. | 361/120 |
| 2007/0264158 | A1 | | 11/2007 | Schmidt et al. | |
| 2008/0034839 | A1 | | 2/2008 | Ante et al. | |
| 2008/0283398 | A1 | | 11/2008 | Nelson et al. | |
| 2010/0000404 | A1 | * | 1/2010 | Sakuma et al. | 95/3 |
| 2010/0229724 | A1 | * | 9/2010 | Tokuda et al. | 96/19 |

FOREIGN PATENT DOCUMENTS

| EP | 1914537 A1 | 4/2008 | |
| EP | 1921437 A2 | 5/2008 | |
| EP | 2141482 A1 | 1/2010 | |
| JP | 63286753 A | 11/1988 | |
| JP | 6-63444 A * | 3/1994 | 96/99 |
| JP | 2004170287 A | 6/2004 | |
| JP | 2006-266961 A | 10/2006 | |

(Continued)

*Primary Examiner* — Richard L Chiesa
(74) *Attorney, Agent, or Firm* — Arent Fox LLP

(57) ABSTRACT

A PM sensor is provided having high responsiveness and capable of long term detection. A PM sensor includes a sensor element that has particulate collection electrodes to which a particulate collection voltage for causing particulate matter contained in exhaust to adhere to a sensor element is applied, and measurement electrodes to which a measurement voltage for measuring an electrical characteristic of the sensor element is applied, in which, after a particulate collection voltage is applied to the particulate collection electrodes application of the particulate collection voltage is stopped in response to a predetermined condition being satisfied, the measurement voltage is applied to the measurement electrodes and the electrical characteristic of the sensor element is measured.

5 Claims, 12 Drawing Sheets

FOREIGN PATENT DOCUMENTS

| | | |
|---|---|---|
| JP | 2008-139294 A | 6/2008 |
| JP | 2008-190502 A | 8/2008 |
| WO | WO-2005124313 A1 | 12/2005 |
| WO | WO-2008111403 A1 | 9/2008 |
| WO | WO-2008111677 A1 | 9/2008 |
| WO | WO-2008117853 A1 | 10/2008 |

* cited by examiner

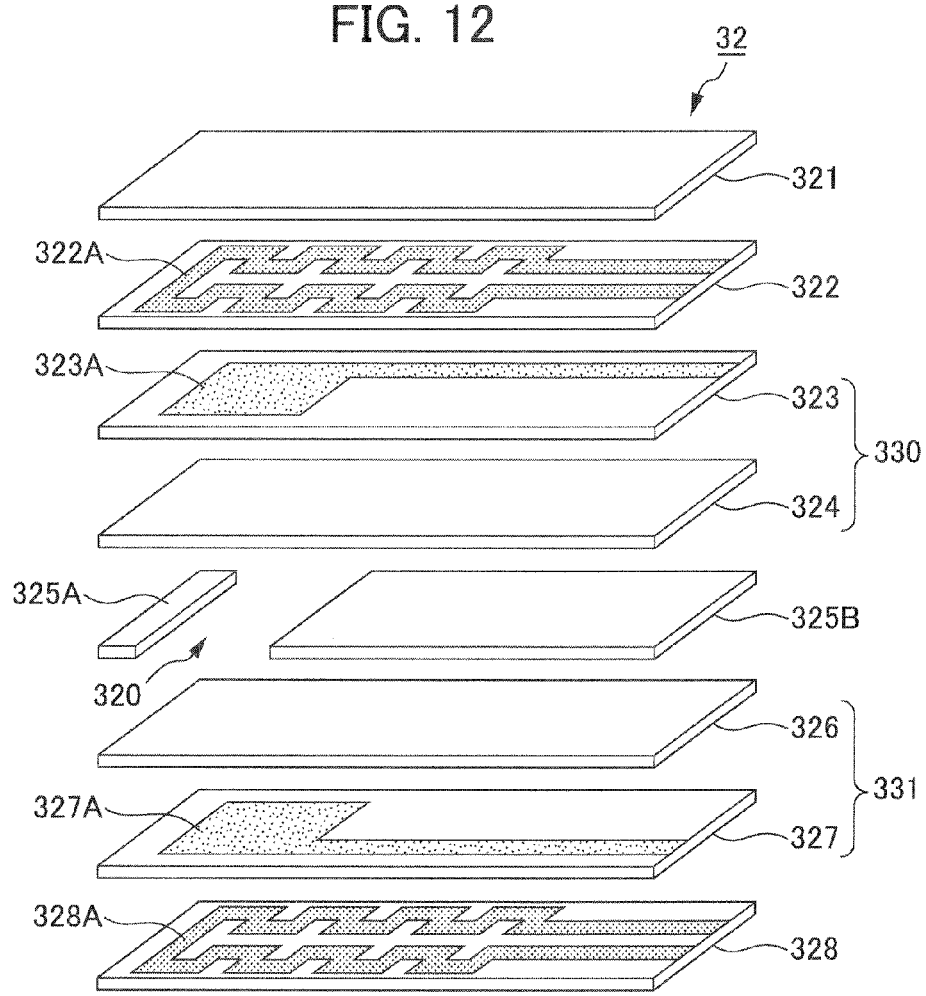
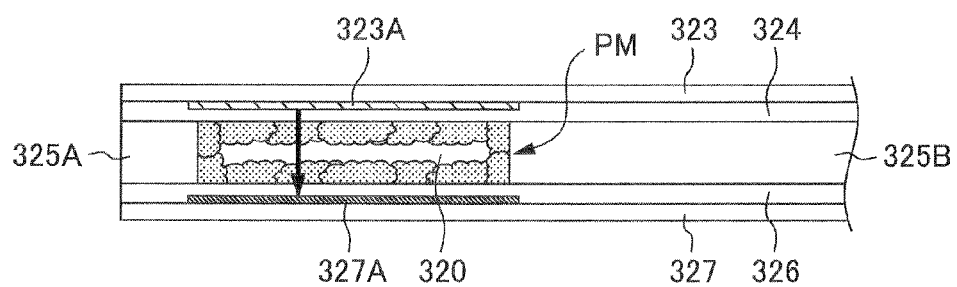

PARTICULATE MATTER DETECTION DEVICE

This application is based on and claims the benefit of priority from Japanese Patent Application No. 2009-032954, filed on 16 Feb. 2009, the content of which is incorporated herein by reference.

BACKGROUND OF THE INVENTION

1. Field of the Invention

The present invention relates to a particulate matter detection device. In particular, it relates to a particulate matter detection device that detects a concentration of particulate matter of exhaust emitted from an internal combustion engine.

2. Related Art

Conventionally, a particulate matter detection device has been provided in the exhaust pipe of an internal combustion engine for detecting a concentration of particulate matter (hereinafter also referred to as PM) in exhaust. For example, a particulate matter detection device has been disclosed, in which a particulate matter detection electrode is configured from a porous electrically conductive material having a predetermined electrical resistance value, that detects an amount of particulate matter in exhaust by measuring a change in an electrical resistance value brought about by particulate matter adhering to this detection electrode (refer to Japanese Unexamined Patent Application, Publication No. 2006-266961).

In addition, a PM emission detection device has been disclosed that can continuously detect a PM amount in exhaust by sequentially regenerating a PM sensor, and detecting a PM amount in exhaust by way of a PM sensor other than the PM sensor undergoing regeneration (refer to Japanese Unexamined Patent Application, Publication No. 2008-190502). This PM sensor has an insulated structure in which electrodes are disposed alternately, and a PM amount in exhaust is detected based on an output value (current value) of the PM sensor by adopting a property in that the electrical resistance value becomes small due to PM conducting when adhering and depositing on the electrode (refer to Japanese Unexamined Patent Application, Publication No. 2008-190502).

In addition, a particulate matter detection device has been disclosed that is mounted in an exhaust pipe, and measures an electrical characteristic of an electrode unit after particulate matter in the exhaust has adhered to the electrode unit by applying a predetermined voltage to the electrode unit, and detects the amount (concentration) of particulate matter in the exhaust from the electrical characteristic thus measured (refer to Japanese Unexamined Patent Application, Publication No. 2008-139294).

SUMMARY OF THE INVENTION

According to the above, in the devices disclosed in Japanese Unexamined Patent Application, Publication No. 2006-266961 and Japanese Unexamined Patent Application, Publication No. 2008-190502, a PM amount in exhaust is detected based on a change in an electrical characteristic of an electrode unit brought about by PM adhering to the electrode unit. However, the change in electrical characteristic of the electrode unit due to PM adhering thereto is not apparent in a state where a PM deposition amount adhered to the electrode unit is thin and exists sparsely, and is first apparent due to PM depositing over the entire surface of the electrode unit. In addition, in a steady operation state of a vehicle or the like, a long time is required (e.g., on the order of 1 to 2 hours) until a change in the electrical characteristic of the electrode unit by PM depositing over the entire surface of the electrode unit is noticeable. As a result, in the devices disclosed in Japanese Unexamined Patent Application, Publication No. 2006-266961 and Japanese Unexamined Patent Application, Publication No. 2008-190502, a long time is required until a PM amount in exhaust is detected, and since the responsiveness relating to time is low, it is not easy to equip in a vehicle or the like.

In addition, according to the above, in the device disclosed in Japanese Unexamined Patent Application, Publication No. 2008-139294, the electrical characteristic of the electrode unit is measured after electrostatically collecting particulate matter in the exhaust to the electrode unit by applying a predetermined voltage to the electrode unit, and detects the amount (concentration) of particulate matter in the exhaust from the electrical characteristic thus measured. In other words, it is possible to detect a change in electrical characteristic in a short period of time by forcibly causing particulate matter in the exhaust to adhere to the electrode unit by applying a predetermined voltage to the electrode unit.

However, there is a problem in that the change in electrical characteristic of the electrode unit brought about by PM deposition no longer occurs when the amount of PM deposition increases excessively. In other words, in the device disclosed in Japanese Unexamined Patent Application, Publication No. 2008-139294, as a result of performing electrostatic particulate collection in a short time period by applying voltage to the electrode unit, the time in which a change in electrical characteristic of the electrode unit is observed is short, and it is not possible to perform measurement over a long period of time. In addition, while electrostatically collecting particulates in a short time period, in a case of a cluster of PM breaking off from a diesel particulate filter (DPF) or the like and adhering to the electrode unit, for example, the PM amount in the exhaust may be detected erroneously.

Furthermore, since electrostatic particulate collection is performed by applying voltage to the electrode unit, the amount of PM deposition increases in a short time and the change in electrical characteristic is not brought about, whereby it is necessary to perform many repetitions of a process with a sequence of particulate collection, measurement, and regeneration. As a result, a number of times applying voltage in order to perform electrostatic particulate collection and a number of times of applying voltage to a heater for regeneration increase, and thus there is a problem in that the amount of power consumption is large.

The present invention was made by taking the above issues into account, and an object thereof is to provide a particulate matter detection device, where the particulate matter detection device detects a concentration of particulate matter in exhaust based on an electrical characteristic of particulate matter, that has high responsiveness and can detect over a long time period.

According to a first aspect of the present invention for achieving the above object, in a particulate matter detection device 11 provided in an exhaust path of an internal combustion engine, including a sensor element 12 to which particulate matter contained in exhaust adheres, and detecting a concentration of particulate matter in exhaust based on an electrical characteristic of the sensor element, the sensor element includes a first electrode unit (123A and 128A) to which a particulate collection voltage for causing particulate matter contained in exhaust to adhere to the sensor element is applied, and second electrode unit (127A and 127B) to which a measurement voltage for measuring an electrical characteristic of the sensor element is applied, and the particulate matter detection device includes: a voltage application start means (13 and, 16) for starting application of particulate collection voltage to the first electrode unit; a first measurement means (14 and, 16) for measuring the electrical characteristic of the sensor element by applying measurement voltage to the second electrode unit, after the application of the particulate collection voltage has started; a voltage application stop means (13 and 16) for stopping application of particulate collection voltage to the first electrode unit in response to a predetermined condition being satisfied; a second measurement means (14 and 16) for measuring the electrical characteristic of the sensor element by applying measurement voltage to the second electrode unit, after stopping application of the particulate collection voltage; and a concentration detection means (16) for detecting a concentration of particulate matter in the exhaust based on a measurement value of the second measurement means.

According to a second aspect of the present invention, in the particulate detection device as described in the first aspect, the first measurement means and the second measurement means are means for applying a measurement voltage of an alternating current to the second electrode unit, and when a frequency of a measurement voltage applied to the second electrode unit by the first measurement means is set as a first frequency, and a frequency of a measurement voltage applied to the second electrode unit by the second measurement means is set as a second frequency, the second frequency is higher than the first frequency.

According to a third aspect of the present invention, the particulate matter detection device as described in the first or second aspect further includes a transient operation state determination means for determining whether an operation state of the internal combustion engine is a transient operation state, in which the concentration detection means starts application of the particulate collection voltage by the voltage application start means in a case where the transient operation state determination means determines a transient operation state.

According to a fourth aspect of the present invention, in the particulate matter detection device as described in any one of the first to third aspects, the particulate collection voltage is large compared to the measurement voltage.

According to a fifth aspect of the present invention, in a particulate matter detection device provided in an exhaust path of an internal combustion engine, including a sensor element to which particulate matter contained in exhaust adheres, and detecting a concentration of particulate matter in exhaust based on an electrical characteristic of the sensor element, the sensor element includes an electrode unit to which any of a particulate collection voltage for causing particulate matter contained in exhaust to adhere to the sensor element, and a measurement voltage, which is small compared to the particulate collection voltage, for measuring an electrical characteristic of the sensor element, are selectively applied, and the particulate matter detection device includes: a voltage application means for applying a particulate collection voltage over a predetermined time period to the electrode unit; a first measurement means for measuring an electrical characteristic of the sensor element by applying measurement voltage to the electrode unit, after the particulate collection voltage has been applied; a determination means for determining whether a predetermined condition has been satisfied; a second measurement means for measuring the electrical characteristic of the sensor element by applying a measurement voltage to the electrode unit, after the predetermined condition has been determined to be satisfied; and a concentration detection means for detecting a concentration of particulate matter in exhaust based on a measurement value of the second measurement means.

According to a sixth aspect of the present invention, in the particulate detection device as described in the fifth aspect, application of the particulate collection voltage by the voltage application means and measurement by the first measurement means are performed again in a case where the determination means determines that the predetermined condition has not been satisfied.

According to a seventh aspect of the present invention, in the particulate matter detection device as described in the fifth or sixth aspect, the first measurement means and the second measurement means are means for applying a measurement voltage of an alternating current to the electrode unit, and when a frequency of a measurement voltage applied to the electrode unit by the first measurement means is set as a first frequency, and a frequency of a measurement voltage applied to the electrode unit by the second measurement means is set as a second frequency, the second frequency is higher than the first frequency.

According to an eighth aspect of the present invention, the particulate matter detection device as described in any one of the fifth to seventh aspects further includes a transient operation state determination means for determining whether an operation state of the internal combustion engine is a transient operation state, in which the concentration detection means applies the particulate collection voltage by the voltage application means in a case where the transient operation state determination means determines a transient operation state.

According to a ninth aspect of the present invention, in the particulate matter detection device as described in any one of the first to eighth aspects, the predetermined condition is whether a value calculated based on the measurement value of the first measurement means exceeds a predetermined threshold value.

According to the invention as described in the first aspect, after particulate collection voltage is applied to the first electrode unit, the application of particulate collection voltage is stopped in response to a predetermined condition being satisfied, the measurement voltage is applied to the second electrode unit, and the electrical characteristic of the sensor element is measured.

Here, a characteristic that does not change until particulate matter of a sufficient amount adheres to the sensor element, while changing even if the deposited amount of particulate matter thus adhered becomes excessive, may be an electrical characteristic of the sensor element.

Contrarily, in the present invention, it is possible to cause particulate matter of a sufficient amount to adhere to the sensor element in a short time, and a state in which a change in electrical characteristic of the sensor element is apparent can be induced at an early stage by applying particulate collection voltage to the first electrode unit. As a result, the concentration of particulate matter contained in exhaust can be detected in as short time as 30 seconds, for example. That is, since the responsiveness is high, it is possible to detect the concentration of particulate matter contained in exhaust at an arbitrary timing while driving a vehicle.

In addition, when the concentration of particulate matter contained in exhaust is being detected, since application of a particulate collection voltage to the first electrode unit is not performed, the concentration of particulate matter can be detected over a long time period due to the particulate matter slowly and spontaneously adhering to the sensor element and the electrical characteristic of the sensor element slowly changing.

Furthermore, in the present invention, since two electrode units, the first electrode unit and the second electrode unit, are provided, it is possible to measure the electrical characteristic of the sensor element by performing collection of particulate matter by way of applying particulate collection voltage to the first electrode while applying measurement voltage to the second electrode unit. As a result, the above effects can be expected also due to being able to determine with good accuracy the stop timing of particulate collection in real time.

In addition, since the concentration of particulate matter can be detected over a long time period, a number of times repeating steps of particulate collection, measurement, and regeneration can be reduced, and thus electric power consumption associated with applying voltage for particulate collection and to the heater can be reduced.

According to the invention as described in the second aspect, a measurement voltage applied by way of the first measurement means and the second measurement means is set as a measurement voltage of alternating current, and a frequency of the measurement voltage employed by the first measurement means is set to be lower than a frequency of the measurement voltage employed by the second measurement means.

Here, the electrical characteristic of the particulate matter is a characteristic that changes according to the frequency of the measurement voltage employed in detection. More specifically, in a case where a low frequency voltage is used as the measurement voltage, a large change in the electrical characteristic occurs even if the deposition of particulate matter to the sensor element is a small amount, whereas a change in the electrical characteristic becomes unnoticeable if the deposition of particulate matter is a large amount. Contrary to this, a case of using a high frequency voltage as the measurement voltage has characteristics in that the measureable range is wide and a large change in electrical characteristic occurs even if the deposition of particulate matter to the sensor element is a large amount, whereas the change in electrical characteristic is small when the deposition of particulate matter is a small amount.

In the present invention, the above described characteristic is adopted, and since particulate collection is stopped according to the electrical characteristic measured with the low frequency voltage, particulate collection can be stopped at an earlier stage, and it is possible to carry out detection of the concentration of particulate matter contained in the exhaust more quickly.

In addition, after stopping particulate collection, it is possible to measure even in a case where particulate matter of a large amount has adhered to the sensor element, due to detection of the concentration of particulate matter in the exhaust being performed based on an electrical characteristic measured with a high frequency voltage. As a result, the measureable time period can be ensured to be long, and together with shortening of the particulate collection time due to using the above-mentioned low frequency voltage, the PM concentration can be detected over a longer time.

In addition, the number of times repeating steps of particulate collection, measurement, and regeneration can be reduced, with the aim of further reducing power consumption.

According to the invention as described in the third aspect, particulate collection voltage is applied to the first electrode unit in a transient operation state, i.e. in a state in which the emitted amount of particulate matter is large. Due to this, particulate matter of a sufficient amount can be adhered to the sensor element in a short time; therefore, it is possible to create a state in which a change in electrical characteristic of the sensor element is apparent at an early stage, and thus the concentration of particulate matter contained in exhaust can be detected more quickly. Consequently, the PM concentration can be detected over a longer time period.

According to the invention as described in the fourth aspect, the particulate collection voltage is large relative to the measurement voltage. For example, as the particulate collection voltage, a high voltage on the order of 2 kV is required, whereas the measurement voltage is sufficient at a low voltage of approximately 1 V. Therefore, according to the present invention, power consumption can be further reduced since the application time of the particulate collection voltage, which is large relative to the measurement voltage, can be shortened.

According to the invention as described in the fifth to eighth aspects, except for effects due to providing two electrode units, effects similar to the effects described above are achieved.

According to the invention as described in the ninth aspect, the application of particulate collection voltage is stopped or the second measure is executed according to whether a value calculated based on a measurement value of the first measurement means has exceeded a predetermined threshold value. As a result, the effects described above are achieved more reliably.

BRIEF DESCRIPTION OF THE DRAWINGS

FIG. 12 is an exploded perspective view of a sensor element 32;

FIG. 13 is a view illustrating a PM detection mechanism of the sensor element 32;

DETAILED DESCRIPTION OF THE INVENTION

Figure 1:
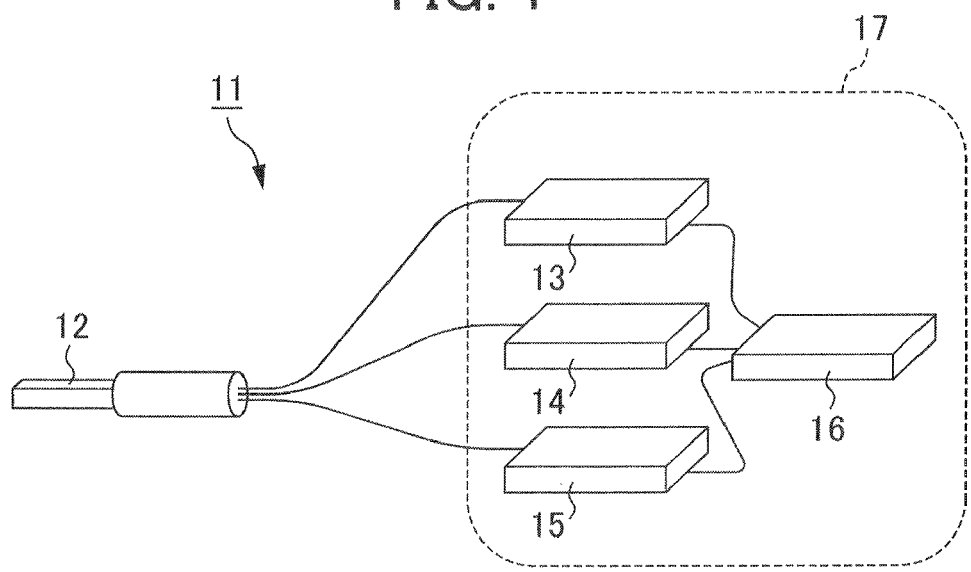
FIG. 1 is a view showing a configuration of a particulate matter detection device related to an embodiment of the present invention.

Hereinafter, embodiments of the present invention are explained in detail while referring to the drawings. It should be noted that, for configurations common to the first embodiment in the description of the second embodiment thereafter, descriptions are omitted.

First Embodiment

FIG. 1 is a view showing a configuration of a particulate matter detection device (hereinafter referred to as "PM sensor") 11 related to the first embodiment.

The PM sensor 11 includes a sensor element 12 provided in an exhaust path of an internal combustion engine (hereinafter referred to as "engine"), and a sensor control unit 17 that is connected to this sensor element 12; the sensor control unit 17 is configured to include a DC power source 13 for particulate collection, an impedance measuring instrument 14, a temperature control device 15 that controls the temperature of the sensor element 12, and an electronic control unit (hereinafter referred to as "ECU") 16 that control these.

Hereinafter, as explained in detail, the PM sensor 11 measures an electrical characteristic of a sensor element 12 to which particulate matter (hereinafter referred to as "PM") contained in exhaust flowing in an exhaust path of the engine is adhered, and detects a concentration of particulate matter (hereinafter referred to as "PM concentration") in the exhaust flowing in the exhaust path based on the electrical characteristic thus measured.

Figure 2:
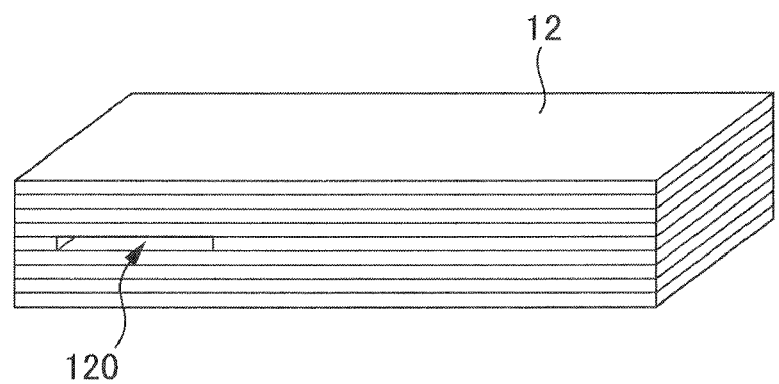
FIG. 2 is a perspective view of a sensor element 12.

FIG. 2 is a perspective view of the sensor element 12. As shown in FIG. 2, the sensor element 12 includes a vent through which exhaust containing PM passes, and a particulate collection portion 120 is formed by this vent. The PM contained in the exhaust adheres and deposits on an inner wall of this particulate collection portions 120.

It should be noted that, in the present embodiment, the electrical characteristic of the sensor element 12 is obtained by measuring the electrical characteristic of the particulate collection portion 120. That is, capacitance of the particulate collection portion 120 indicates a capacitance of the sensor element 12 in the description below.

Figure 3:
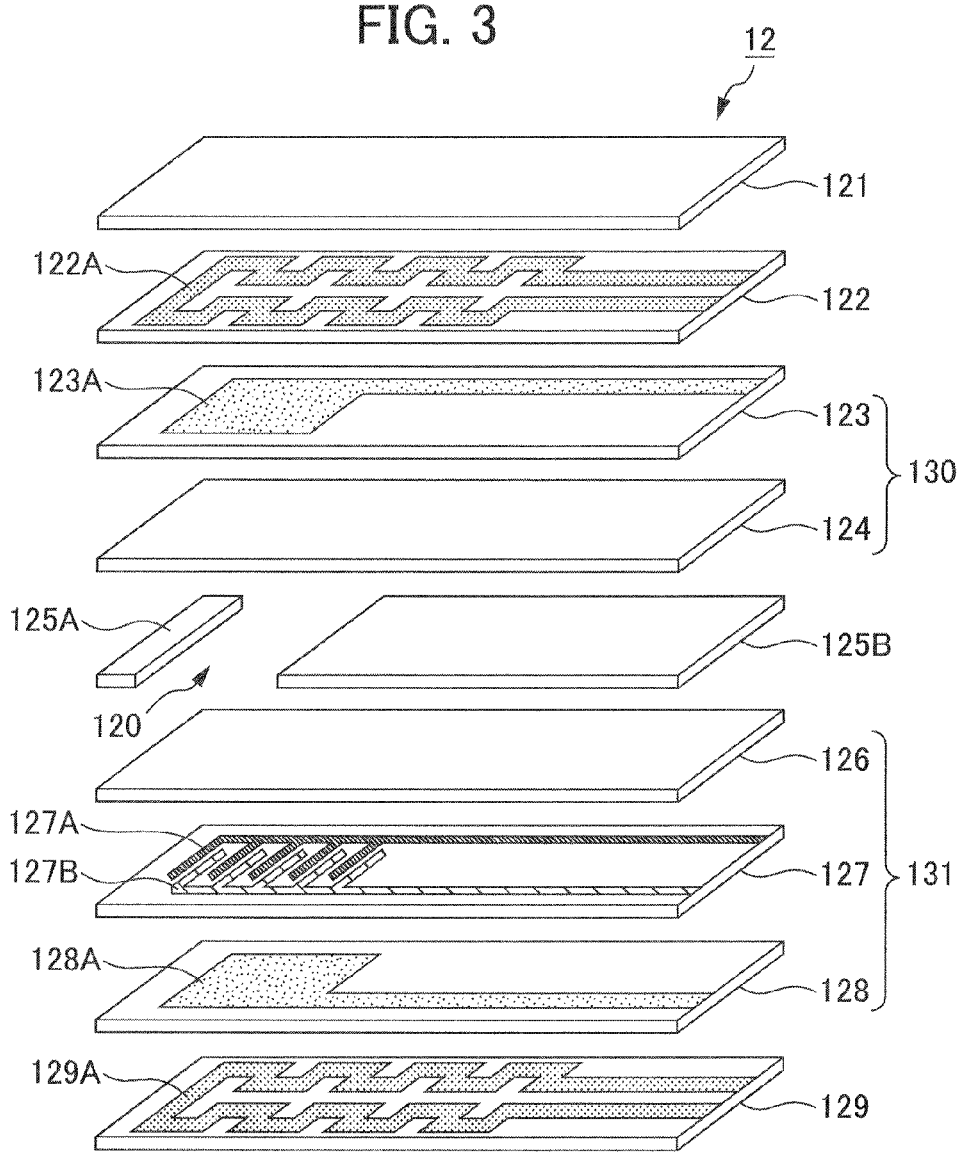
FIG. 3 is an exploded perspective view of the sensor element 12.

FIG. 3 is an exploded perspective view of the sensor element 12. As shown in FIG. 3, the sensor element 12 is configured by combining a pair of electrode plates 130 and 131 by way of setting spacers 125A and 125B of plate shape therebetween, and sandwiching with heater layers 122 and 129 and an alumina plate 121. As a result, a particulate collection portion 120 surrounded by the electrode plates 130 and 131 and spacers 125A and 125B is formed.

The electrode plate 130 is formed by laminating a dielectric layer 124 and a particulate collection electrode layer 123. In addition, the electrode plate 131 is formed by laminating a dielectric layer 126, a measurement electrode layer 127, and a particulate collection electrode layer 128.

The measurement electrode layer 127 is provided with a pair of comb-shaped measurement electrodes 127A and 127B. More specifically, the measurement electrodes 127A and 127B are configured to include a pair of comb-teeth portions formed at a position corresponding to the particulate collection portion 120 on an end side of the measurement electrode layer 127, and a pair of comb body portions that extend from these comb-teeth portions to another end side. More specifically, the measurement electrodes 127A and 127B are opposingly disposed so that the comb-teeth portions of one of the comb-shaped electrodes 127A and the comb-teeth portions of the other comb-shaped electrode 127B are fit between each other.

In addition, the pair of comb body portions is electrically connected to the impedance measuring instrument 14.

Here, a PM detection mechanism of the present embodiment provided with comb-shaped measurement electrodes 127A and 127B in the measurement electrode layer 127 is described.

Figure 4:
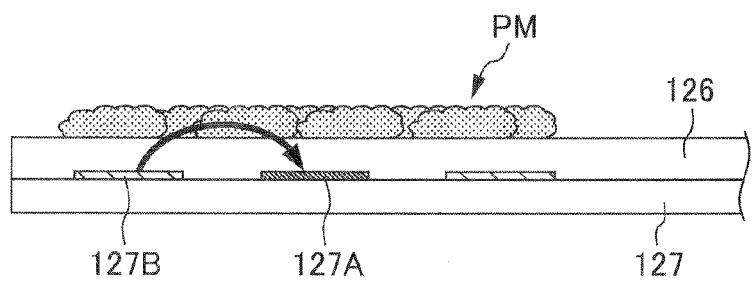
FIG. 4 is a view illustrating a PM detection mechanism of the sensor element 12.

FIG. 4 is a view schematically showing an appearance when PM adheres and deposits entirely inside the particulate collection portion 120 of the sensor element 12 of the present embodiment. As shown in FIG. 4, PM collected in the particulate collection portion 120 deposits via the dielectric layer on the comb-teeth portions of comb-shaped measurement electrodes 127A and 127B. At this time, a leak electric field between the measurement electrode 127A and 127B, which are adjacent, is influenced by PM thus deposited, and the electrical characteristic between the measurement electrodes 127A and 127B changes. Since this change in electrical characteristic has a correlation with PM deposition amount, it is possible to detect PM by detecting this change in electrical characteristic.

Particulate collection electrode layers 123 and 128 are provided with particulate collection electrodes 123A and 128A, which are made from a tungsten conductor layer. These particulate collection electrodes 123A and 128A are configured to include a conductor portion formed in a substantially square shape at a position corresponding to the particulate collection portion 120 on an end side of the particulate collection electrode layers 123 and 128, and a conductive wire portion that linearly extends from this conductor portion to the other end side of the alumina plate.

In addition, the conductive wire portion of the particulate collection electrodes 123A and 128A are electrically connected to a DC power source 13 for particulate collection.

It should be noted that the length of a side of the conductor portion of the particulate collection portions 123A and 128A is approximately 10 mm.

The heater layer 122 and 129 are provided with heater wires 122A and 129A, and these heater wires 122A and 129A are electrically connected to the temperature control device 15.

In addition, the alumina plate 121 is an alumina plate of substantially rectangular shape, and the thickness is approximately 1 mm.

The DC power source 13 for particulate collection is electrically connected to the conductive wire portion of the particulate collection electrodes 123A and 128A provided to the particulate collection electrode layers 123 and 128, via a change-over switch (not illustrated). The DC power source 13 for particulate collection operates based on a control signal sent from the ECU 16, and applies a predetermined particulate collection voltage that is greater than the measurement voltage, which is mentioned later, over the particulate collection electrode layers 123 and 128. As a result, PM in the exhaust is made to adhere to the particulate collection portion 120.

It should be noted that the change-over switch operates based on a control signal sent from the ECU 16.

The impedance measuring instrument 14 is electrically connected to the pair of comb body portions of the measurement electrode layer 127 via the change-over switch (not illustrated). The impedance measuring instrument 14 operates based on a control signal sent from the ECU 16, and detects a capacitance of the particulate collection portion 120 with a predetermined measurement voltage and measurement cycle, and outputs a detection signal substantially proportional to the capacitance thus detected.

It should be noted that the change-over switch operates based on a control signal sent from the ECU 16.

The temperature control device 15 is electrically connected to the heater wires 122A and 129A of the heater layers 122 and 129 provided by adjoining to the electrode plates 130 and 131, respectively, and is configured to contain a DC power source (not illustrated) for the heaters that supplies electric power to these heater layers 122 and 129.

The DC power source for the heaters operates based on a control signal sent from the ECU 16, and conducts a predetermined current to the heater layers 122 and 129. The heater layers 122 and 129 generate heat when current from the power source for the heaters is supplied, and heat each of the electrode plates 130 and 131. As a result, each of the electrode plates 130 and 131 are heated, and PM adhered to the particulate collection portion 120 can be combustively removed, whereby the sensor element 12 can be regenerated.

The ECU 16 shapes an input signal waveform from a variety of sensors, corrects voltage levels to a predetermined level, and is provided with an input circuit having functions such as for converting an analog signal value to a digital signal value, and a central processing unit (hereinafter referred to as "CPU"). Alternatively, the ECU 16 is provided with a storage circuit that stores a variety of operation programs executed by the CPU, operation results, and the like, and an output circuit that outputs control signals to the DC power source 13 for particulate collection, the impedance measuring instrument 14, the temperature control device 15, the change-over switch, and the like.

Figure 5:
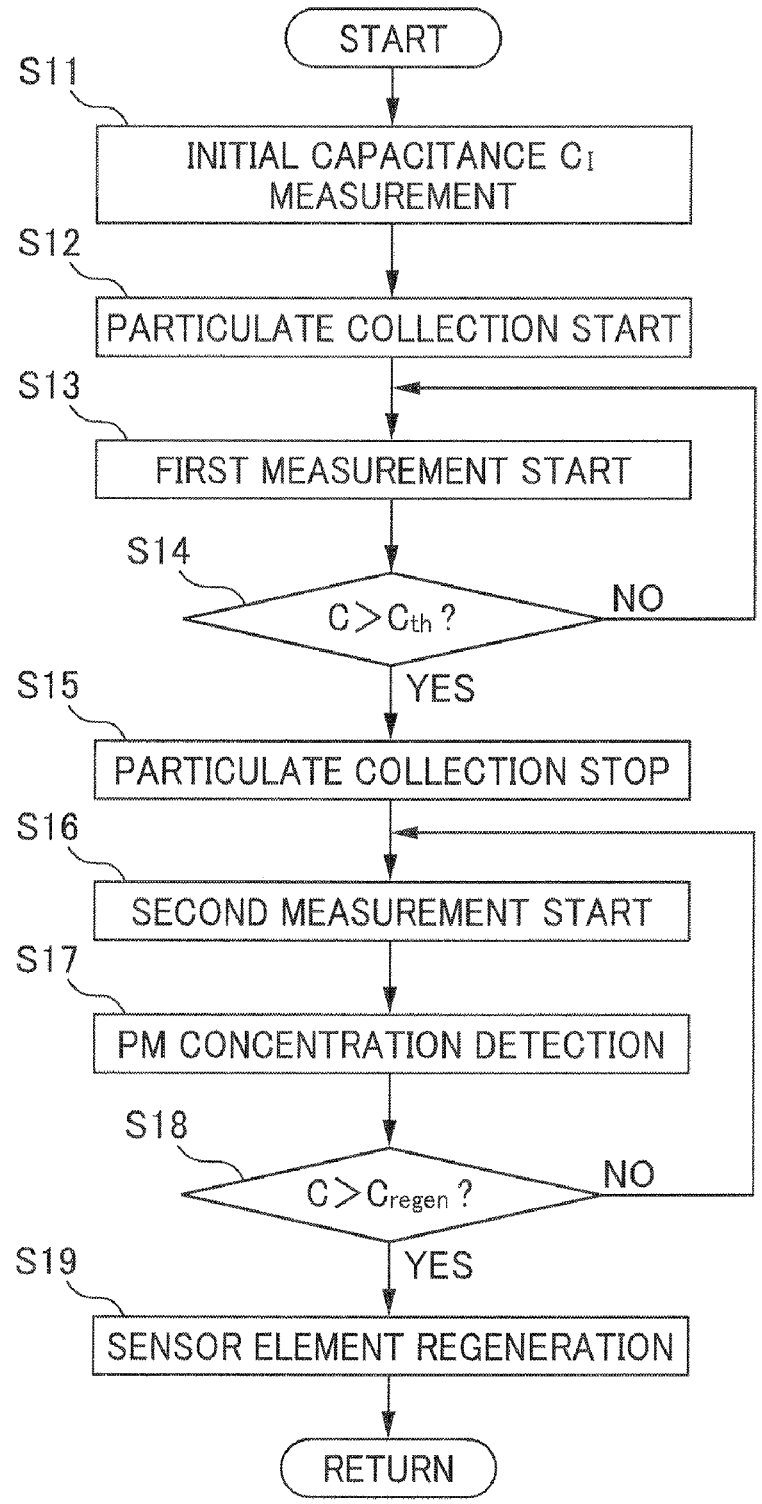
FIG. 5 is a flowchart showing steps of PM concentration detection using a PM sensor 11.

FIG. 5 is a flowchart showing steps of detecting PM concentration of the exhaust using the PM sensor 11. This flowchart is repeatedly carried out by the ECU 16 after engine start-up.

In Step S11, the capacitance of the particulate collection portion 120 is measured, and this is stored as an initial capacitance $C_I$.

In Step S12, particulate collection voltage is applied to the particulate collection electrodes (123A and 128A), and particulate collection is started. As a result, PM contained in the exhaust is adhered to the particulate collection portion 120. The particulate collection voltage is set at 2 kV, for example.

In Step S13, the particulate collection voltage is applied to the particulate collection electrodes (123A and 128A), and a first measurement is started in a state of the particulate collection voltage being applied as before. More specifically, the measurement voltage is applied to the measurement electrodes (127A and 127B), and the capacitance of the particulate collection portion 120 is measured. The measurement voltage is set at 1 V, for example.

In Step S14, it is determined whether the capacitance C measured in the first measurement of Step S13 exceeds a predetermined threshold value $C_{th}$ set in advance. In a case of this determination being YES, the procedure advances to Step S15, and in a case of being NO, Step S13 is repeated and the first measurement is started again.

In Step S15, application of the particulate collection voltage to the particulate collection electrodes (123A and 128A) is stopped, thereby stopping particulate collection. As a result, the adherence of PM due to the application of the particulate collection voltage is stopped.

Here, in the present embodiment, aspects of stopping particulate collection in a case where the capacitance C thus measured in the first measurement, in a state of particulate collection voltage being applied as before, exceeds the predetermined threshold value $C_{th}$ are explained.

Figure 6:
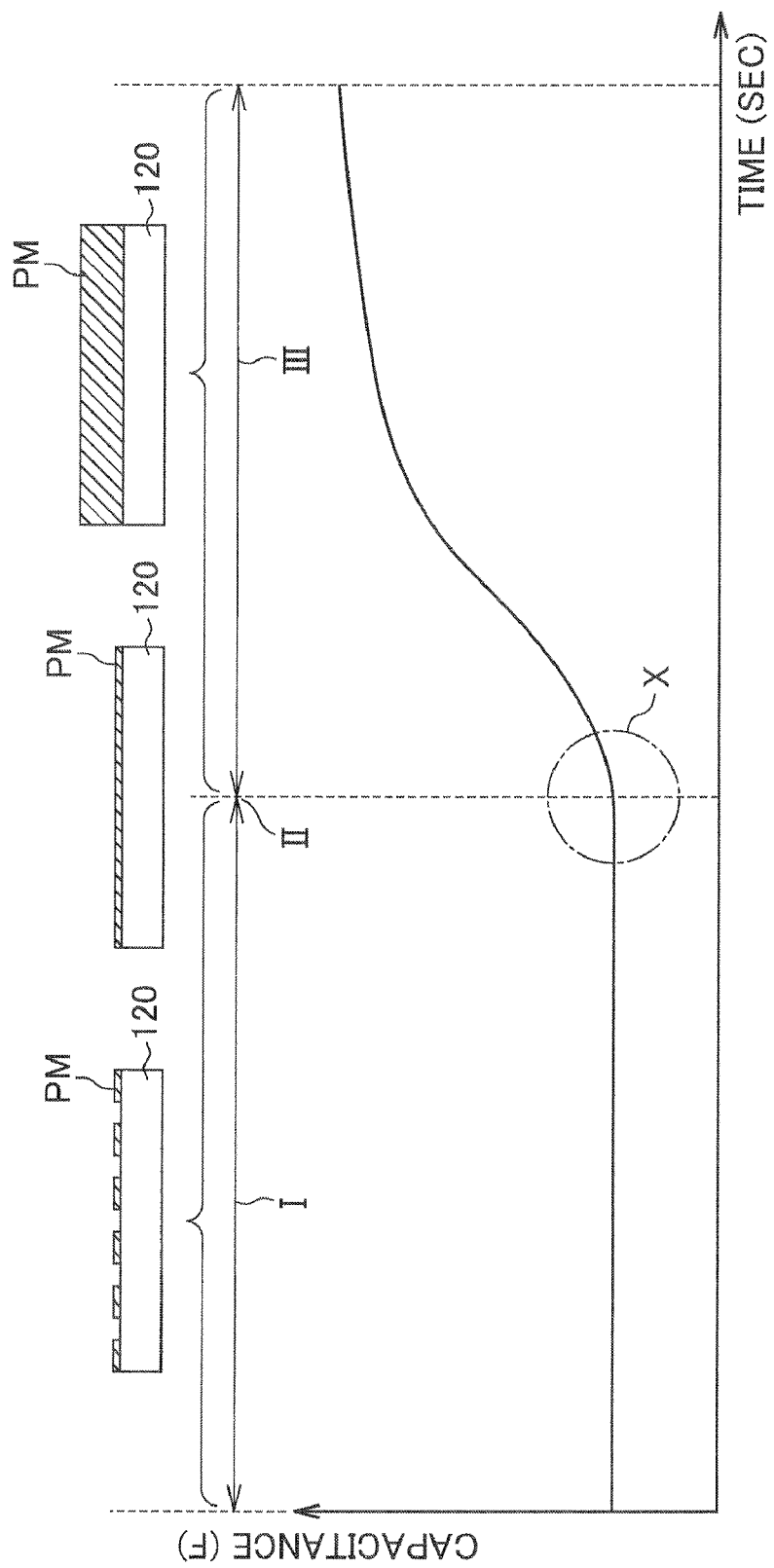
FIG. 6 is a chart illustrating the steps of PM concentration detection using the PM sensor 11.

FIG. 6 is a chart showing a relationship between a PM amount deposited on the particulate collection portion 120 when adhering spontaneously to the particulate collection portion 120 (hereinafter referred to as "spontaneous particulate collection") and a capacitance change (i.e. a capacitance change of the sensor element 12) of the particulate collection portion 120, in a case where particulate collection is carried out using the sensor element 12 without applying the particulate collection voltage. The horizontal axis of FIG. 6 represents time (seconds), and the vertical axis thereof represents capacitance (F).

In region I of FIG. 6, PM gradually deposits on an inner wall of the particulate collection portion 120 with the elapse of time; however, at first, there is only thin sparse deposition; therefore, there is no influence on the electrical characteristic of the particulate collection portion 120, and a change in capacitance is unnoticeable.

In region II, PM begins to thinly deposit entirely on the inner wall of the particulate collection portion 120 with the elapse of time, and as a result of becoming so that an influence on the electrical characteristic of the particulate collection portion 120 is imparted, the capacitance starts to increase.

In region III where time has further elapsed, PM thickly deposits to be dense entirely on the inner wall of the particulate collection portion 120, and as a results of becoming so that a large influence on the electrical characteristic of the particulate collection portion 120 is exerted, the capacitance further increases and before long the capacitance converges at a constant value. That is, a maximum measureable capacitance $C_{max}$ exists for the PM sensor 11.

Incidentally, as shown in FIG. 6, the time of region I, in which a change in capacitance is unnoticeable, is very long. This indicates that, in normal operation of a vehicle, a considerably long time period (e.g., 1 to 2 hours) is necessary until PM deposits entirely on the inner wall of the particulate collection portion 120 by spontaneous particulate collection and a change in capacitance occurs. Consequently, since calculation of PM concentration in exhaust is performed based on the change in capacitance, this means that a long period of time is required in detection of PM concentration.

On the other hand, if the particulate collection voltage is continually applied as is conventionally even after a change in capacitance has been observed, PM will be abundantly deposited, whereby the maximum measureable capacitance $C_{max}$ will be reached in a short time period.

As a result, the PM sensor 11 of the present embodiment promotes deposition of PM by applying the particulate collection voltage, and stops application of the particulate collection voltage to change to spontaneous particulate collection when a change in capacitance comes to be observed, i.e. when the capacitance has exceeded the predetermined threshold value $C_{th}$. Due to this, a condition is made in which the PM concentration in exhaust can be detected in a short time period, as well as long time detection becoming possible.

In addition, the predetermined threshold value $C_{th}$ used in the determination of Step S14 will be explained.

As described above, in order to produce a state in which the PM concentration can be detected in a short time period as well as making long term detection possible, it is preferable to stop the application of particulate collection voltage and switch to spontaneous particulate collection at the moment when a change in capacitance due to PM deposition is observed.

Figure 7:
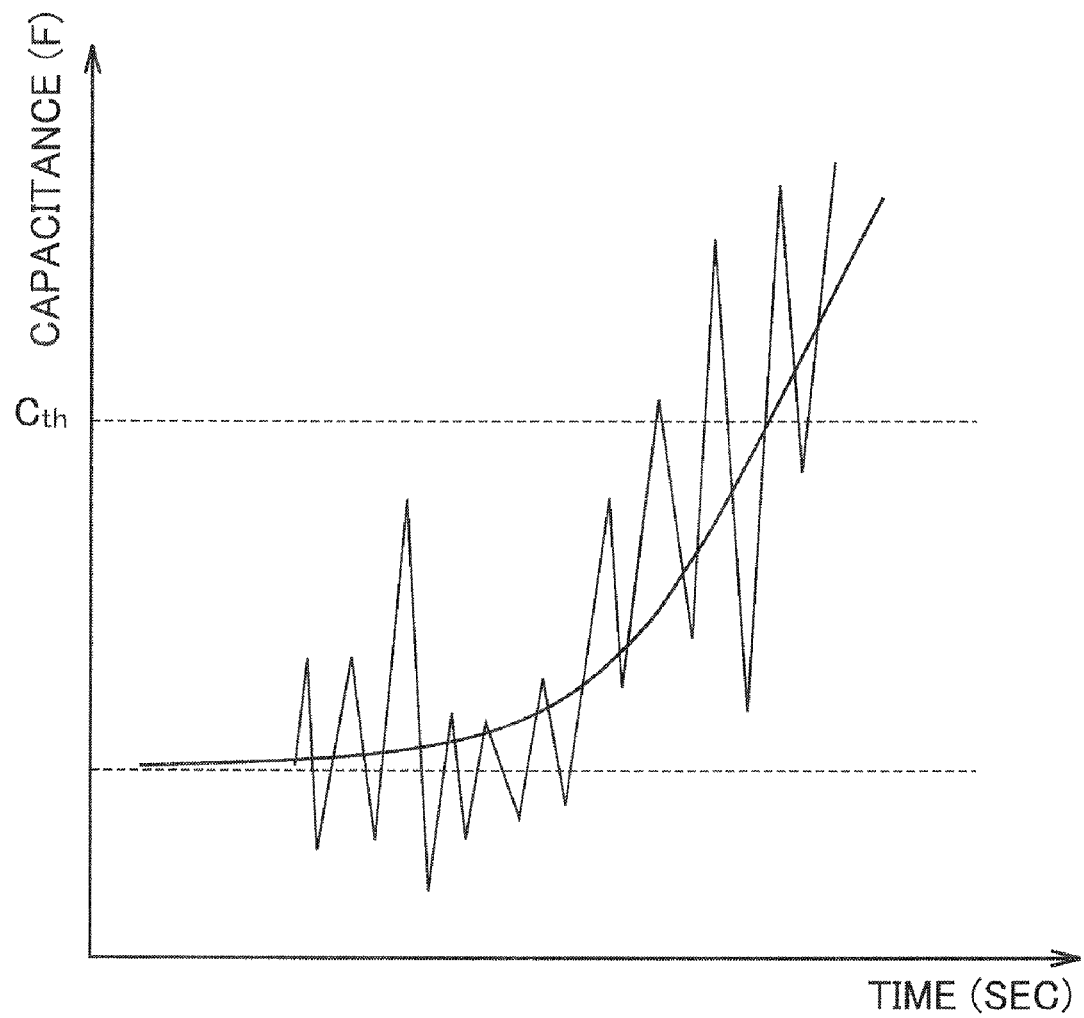
FIG. 7 is a partially enlarged view of X in FIG. 6.

On the other hand, as shown in FIG. 7, which is a partially enlarged view of X in FIG. 6, noise is contained in the detection value. In particular, large noise appears under unfavorable conditions such as in a case where clusters of PM break off from the DPF or the like and adhere to the particulate collection portion 120, and in a case where the electrical property of PM is unstable due to the exhaust temperature being low and the PM temperature being low. As a result, it is necessary to accurately distinguish noise and the change in capacitance due to PM deposition; therefore, a large value relative to the noise values under the most unfavorable conditions is set as the threshold value $C_{th}$.

Referring again to FIG. 5, in Step S16, a second measurement is started. More specifically, measurement voltage is applied to the measurement electrodes (127A and 127B), and the capacitance of the particulate collection portion 120 is measured.

In Step S17, the PM concentration in exhaust is detected. More specifically, a value of the initial capacitance $C_I$ measured in Step S11 subtracted from the capacitance measured in the second measurement of Step S16 is calculated, and this is stored as a variation amount of capacitance $\Delta C$ (i.e. a variation amount of capacitance of the particulate collection portion 120 before and after particulate collection).

Next, the PM concentration in exhaust is detected according to the variation amount of capacitance $\Delta C$. More specifically, the PM concentration according to the variation amount of capacitance $\Delta C$ thus measured is calculated based on a control map that correlates the variation amount of capacitance $\Delta C$ of the particulate collection portion 120 and PM concentration in exhaust. It should be noted that the control map is prepared by performing predetermined experiments beforehand, and is stored in the ECU 16.

Here, a supplementary explanation is provided for detection of PM concentration by way of spontaneous particulate collection carried out in the second measurement.

Figure 8:
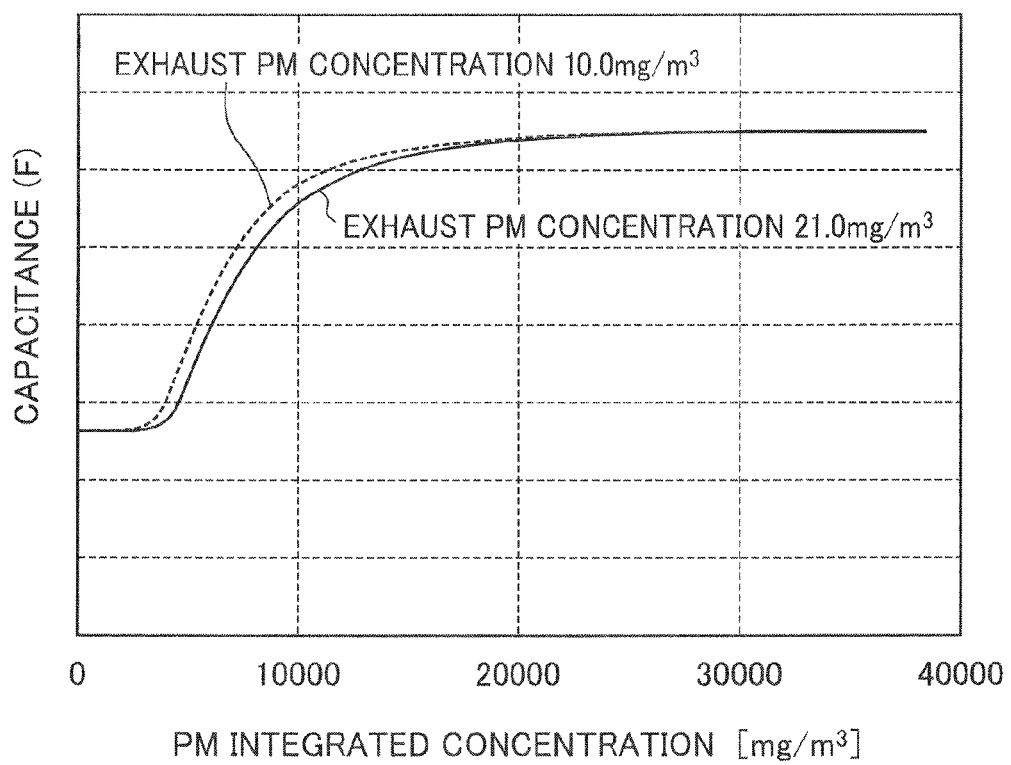
FIG. 8 is a chart illustrating detection of PM concentration by way of spontaneous particulate collection.

FIG. 8 is a chart showing a relationship between capacitance and PM integrated concentration (PM concentration× time) using an exhaust PM concentration of 10.0 mg/m$^3$ and an exhaust PM concentration of 21.0 mg/m$^3$. As shown in FIG. 8, the curved line when the exhaust PM concentration was 10.0 mg/m$^3$ and the curved line when 21.0 mg/m$^3$ are approximately equal. This indicates that, in a case of PM having spontaneously collected, there is a correlation between capacitance and PM deposition amount, and it is possible to detect PM concentration in exhaust by measuring the capacitance.

Referring again to FIG. 5, in Step S18, it is determined whether the capacitance measured in the second measurement of Step S16 exceeds a regeneration determination value $C_{regen}$ of the sensor element 12. Here, the regeneration determination value $C_{regen}$ is a value that is slightly smaller than a maximum measureable capacitance $C_{max}$ of the sensor element 12, and is preferably a value 0.95 times the maximum capacitance $C_{max}$.

In a case of this determination being YES, the procedure advances to Step S19, and in a case of being NO, the procedure returns to Step S16 and starts the second measurement again. It should be noted that, at this time, the sensor element 12 can start the second measurement due to being in a state in which a change in capacitance of the particulate collection portion 120 is apparent.

In Step S19, regeneration of the sensor element 12 is carried out. More specifically, the particulate collection portion 120 is heated by passing a predetermined current to the heater layer to cause heat generation, and PM adhered to the particulate collection portion 120 is combustively removed.

According to the present embodiment, after particulate collection voltage is applied to the particulate collection electrodes 123A and 128A, according to whether a predetermined condition has been satisfied, the measurement voltage is applied to the measurement electrodes 127A and 127B while the application of particulate collection voltage is stopped, and the capacitance of the particulate collection portion 120 is measured.

Here, there is a characteristic in the capacitance of the particulate collection portion 120 that does not change until particulate matter adheres entirely over the particulate collection portion 120, and that does not change even if the deposited amount of particulate matter thus adhered to the particulate collection portion 120 becomes excessive.

Contrarily, in the present embodiment, PM in the exhaust can be caused to adhere entirely over the particulate collection portion 120 in a short time period, and a state in which a change in the capacitance of the particulate collection portion 120 is apparent can be induced at an early stage, by applying the particulate collection voltage to the particulate collection electrodes 123A and 128A. As a result, the concentration of PM contained in exhaust can be detected in a short time period such as 30 seconds, for example. That is, since the responsiveness is high, the concentration of PM contained in exhaust can be detected at an arbitrary timing while driving the vehicle.

In addition, when the concentration of PM contained in exhaust is detected, since the application of particulate collection voltage to the particulate collection portion 120 is not carried out, PM is slowly and spontaneously adhered to the particulate collection portion 120, and the concentration of PM can be detected over a long time period due to the capacitance of the particulate collection portion the gradually changing.

In addition, in the present embodiment, since the two electrodes of the particulate collection electrodes 123A and 128A, and the measurement electrodes 127A and 127B are provided, the capacitance of the particulate collection portion 120 can be measured by carrying out PM particulate collection by applying particulate collection voltage to the particulate collection electrodes 123A and 128A, while applying measurement voltage to the measurement electrodes 127A and 127B. As a result, the above effects can be expected also due to being able to determine with good accuracy the stop timing of particulate collection in real-time.

In addition, since the concentration of PM can be detected over a long time period, a number of times repeating steps of particulate collection, measurement, and regeneration can be reduced, and thus electric power consumption associated with applying voltage for particulate collection and to the heater can be reduced. Furthermore, the power consumption amount can be reduced also due to shortening the application time of particulate collection voltage, which is different from measurement voltage for which a low voltage of approximately 1 V is sufficient, and requires a high voltage of 2 kV, for example.

In the present embodiment, the particulate collection electrodes 123A and 128A constitute the first electrode unit, the measurement electrodes 127A and 127B constitute the second electrode unit, the DC power source 13 for particulate collection and the ECU 16 constitute the voltage application start means, the impedance measuring instrument 14 and the ECU 16 constitute the first measurement means, the DC power source 13 for particulate collection and the ECU 16 constitute the voltage application stop means, the impedance measuring instrument 14 and the ECU 16 constitute the second measurement means, and the ECU 16 constitutes the concentration detection means.

More specifically, the means related to execution of Step S12 of FIG. 5 constitute the voltage application start means, the means related to execution of Step S13 constitute the first measurement means, the means related to execution of Steps S14 and S15 constitute the voltage application stop means, the means related to execution of Step S16 constitute the second measurement means, and the means related to execution of Step S17 constitute the concentration detection means.

Second Embodiment

The PM sensor related to the second embodiment is a configuration similar to the first embodiment except for the configuration of the ECU 16 of the PM sensor 11 related to the first embodiment, and more specifically, portions constituting the first measurement means and the second measurement means being different.

In addition, similarly to the first embodiment, the electrical characteristic of the sensor element is obtained by measuring the electrical characteristic of the particulate collection portion also in the present embodiment. That is, in the following explanation, the capacitance of the particulate collection portion indicates the capacitance of the sensor element.

Figure 9:
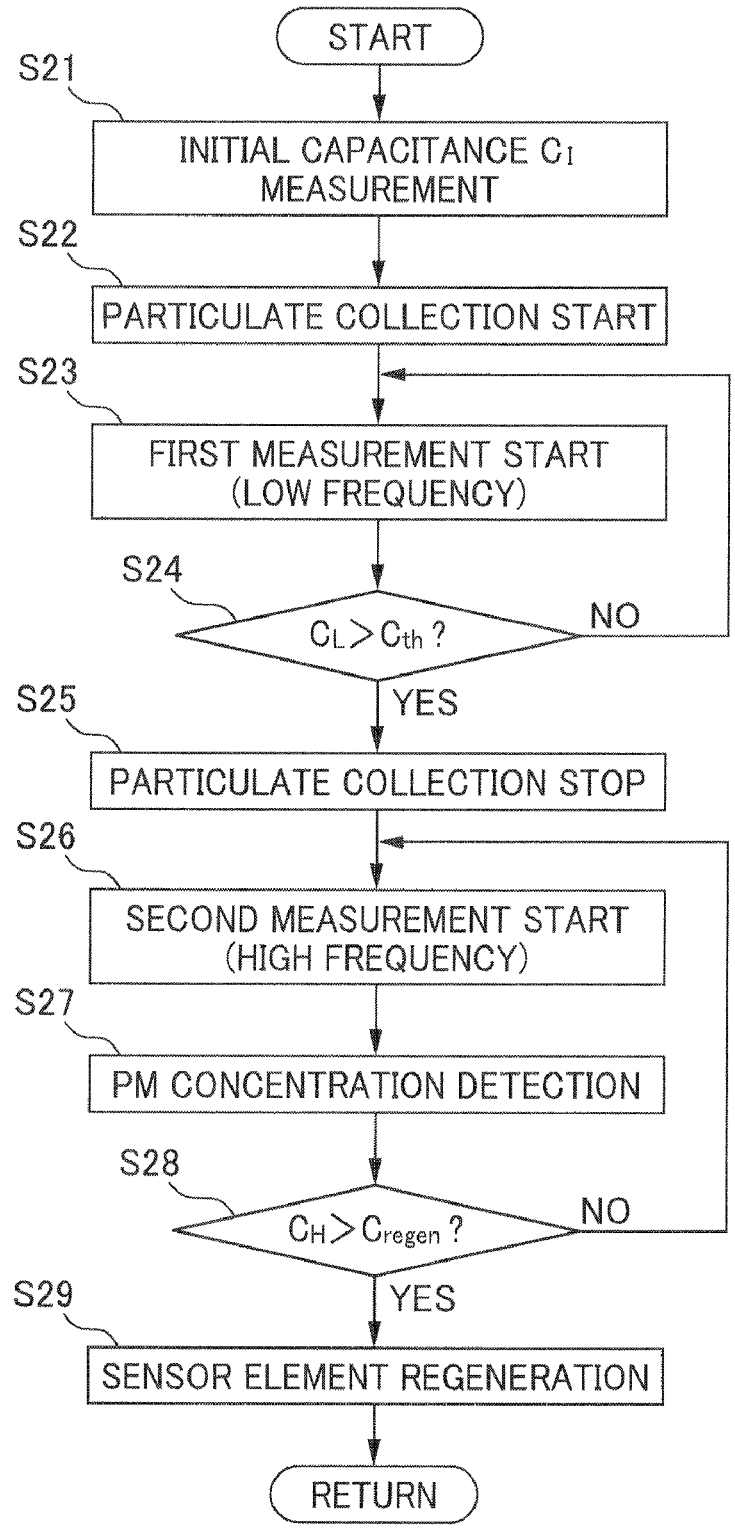
FIG. 9 is a flowchart showing steps of PM concentration detection using a PM sensor 21.

FIG. 9 is a flowchart showing steps of detecting PM concentration in exhaust using the PM sensor 21. This flowchart is repeatedly carried out by the ECU 26 after engine start-up.

In Step S21, the capacitance of the particulate collection portion is measured, and this is stored as the initial capacitance $C_I$.

In Step S22, particulate collection voltage is applied to the particulate collection electrodes, thereby starting particulate collection. Due to this, PM contained in the exhaust is caused to adhere to the particulate collection portion.

In Step S23, the particulate collection voltage is applied to the particulate collection electrodes, and a first measurement is started in a state of the particulate collection voltage being applied as before. More specifically, measurement voltage, of a frequency that is lower than a frequency of the alternating measurement voltage applied in the second measurement described later, is applied to the measurement electrodes, and a capacitance $C_L$ of the particulate collection portion is measured.

In Step S24, it is determined whether the capacitance $C_L$ thus measured in the first measurement of Step S23 exceeds a predetermined threshold value $C_{th}$ set in advance. In a case of the determination being YES, the procedure advances to Step S25, and in a case of being NO, the procedure returns to Step S23 and starts the first measurement again.

In Step S25, the application of particulate collection voltage to the particulate collection electrodes is stopped, thereby stopping particulate collection. As a result, the adherence of PM due to the application of particulate collection voltage is stopped.

In Step S26, a second measurement is started. More specifically, measurement voltage, of a frequency that is higher than a frequency of the measurement voltage applied in the first measurement described above, is applied to the measurement electrodes, and a capacitance $C_H$ of the particulate collection portion is measured.

Here, an aspect of setting the frequency of the alternating measurement voltage used in the first measurement to be lower than the frequency of the measurement voltage used in the second measurement.

Figure 10:
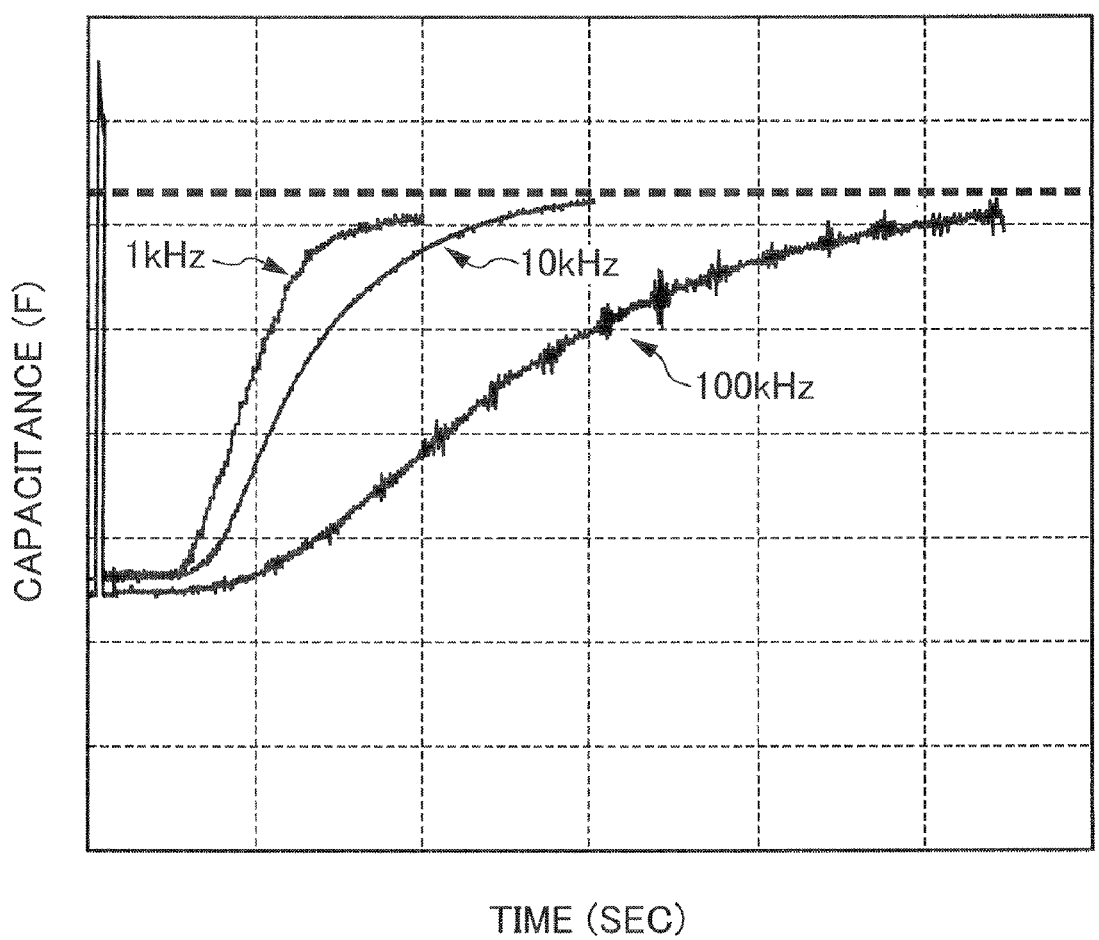
FIG. 10 is a chart illustrating the steps of PM concentration detection using the PM sensor 21.

FIG. 10 is a chart showing a relationship between capacitance and time when the frequency of the measurement voltage is changed. As shown in FIG. 10, the capacitance of the particulate collection portion has a characteristic of being different depending on the frequency of measurement voltage. More specifically, in a case of a low frequency voltage, a change in capacitance occurs even if the deposition of PM in the particulate collection portion is a small amount, whereas in a case of a high frequency voltage, a change in the capacitance occurs even if the deposition of PM in the particulate collection portion is a large amount.

Figure 11:
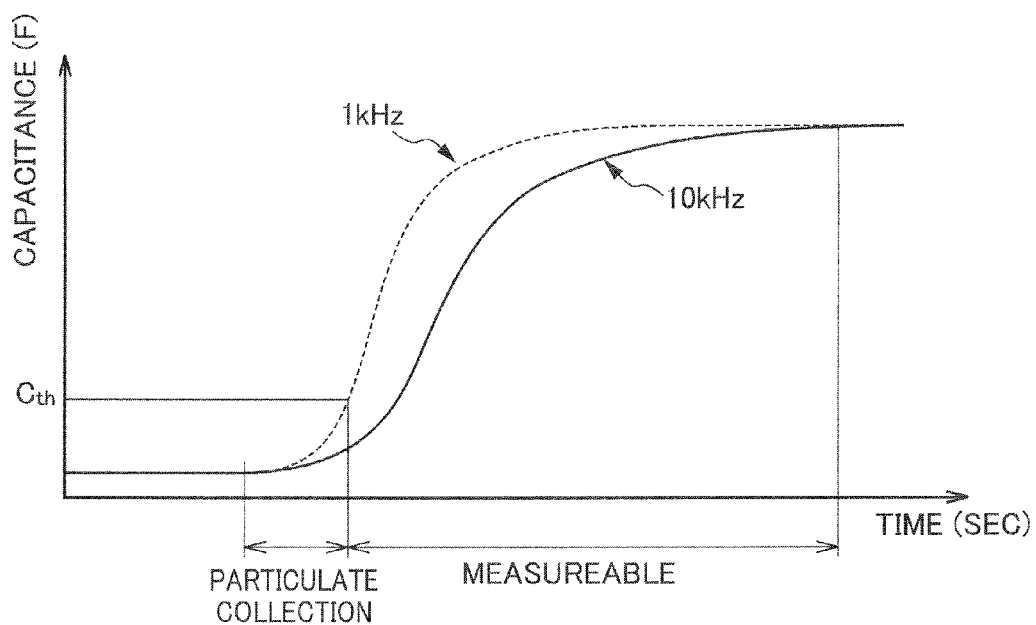
FIG. 11 is a chart illustrating the steps of PM concentration detection using the PM sensor 21.

FIG. 11 is a chart showing a relationship between capacitance and time when using a measurement voltage with a frequency of 1 kHz and a measurement voltage at 10 kHz. As shown in FIG. 11, compared to the high frequency voltage, the low frequency voltage exceeds the threshold value $C_{th}$ used in determination of particulate collection stop in a short time period. As a result, in the present embodiment, it is made possible to stop particulate collection in a shorter time period by determining whether it is a state in which a change in capacitance of the particulate collection portion occurs and PM detection is possible by the capacitance measured using the low frequency voltage. In addition, after the particulate collection stopping, the measureable time can be extended by performing the detection of PM concentration in the exhaust based on the capacitance measured using high frequency voltage, and thus it is made possible to detect PM concentration over a longer time period.

Referring again to FIG. 9, in Step S27, PM concentration in the exhaust is detected.

More specifically, a value is calculated that is the initial capacitance $C_I$ measured in Step S21 subtracted from the capacitance $C_H$ measured in the second measurement of Step S26, and this value is stored as the variation amount of capacitance $\Delta C$ (i.e. the variation amount of capacitance of the particulate collection portion before and after particulate collection).

Next, PM concentration in the exhaust is detected according to the variation amount of capacitance $\Delta C$. More specifically, the PM concentration according to the variation amount of capacitance $\Delta C$ thus measured is calculated based on a control map that correlates variation amount of capacitance $\Delta C$ of the particulate collection portion and PM concentration in the exhaust. It should be noted that the control map is prepared by performing predetermined experiments beforehand, and is stored in the ECU.

In Step S28, it is determined whether the capacitance $C_H$ measured in the second measurement of Step S26 exceeds a regeneration determination value $C_{regen}$ of the sensor element. Here, the regeneration determination value $C_{regen}$ is a value that is slightly smaller than a maximum measureable capacitance $C_{max}$ of the sensor element, and is preferably a value 0.95 times the maximum capacitance $C_{max}$.

In a case of the determination being YES, the procedure advances to Step S29, and in a case of being NO, the procedure returns to Step S26 and starts the second measurement again. It should be noted that, at this time, the sensor element can start the second measurement due to being in a state in which a change in capacitance of the particulate collection portion is apparent.

In Step S29, regeneration of the sensor element is carried out. More specifically, the particulate collection portion is heated by passing a predetermined current to the heater layer to cause heat generation, and PM adhered to the particulate collection portion is combustively removed.

In the present embodiment, the following effects are achieved in addition to the effects of the first embodiment.

According to the present embodiment, the frequency of the alternating measurement voltage used in the first measurement is set to be smaller than the frequency of the measurement voltage used in the second measurement.

Here, there is a characteristic in that the capacitance of PM changes according to the frequency of the measurement voltage used in detection. More specifically, in a case of using a low frequency voltage as the measurement voltage, a large change in capacitance occurs even if the deposition of PM to the particulate collection portion is a small amount, whereas a change in capacitance becomes unnoticeable if the deposition of PM becomes a large amount. Contrary to this, a case of using a high frequency voltage as the measurement voltage has characteristics in that the measureable range is wide and a large change in capacitance occurs even if the deposition of PM to the particulate collection portion is a large amount, whereas the change in capacitance is small when the deposition of PM is a small amount.

In the present invention, the above described characteristic is adopted, and since particulate collection is stopped according to the capacitance measured with the low frequency voltage, particulate collection can be stopped at an earlier stage, and it is possible to carry out detection of the concentration of PM contained in the exhaust more quickly.

In addition, after the particulate collection stopping, measurement is possible even in a case in which a large amount of PM has adhered to the particulate collection portion, by carrying out detection of the concentration of PM in the exhaust based on the capacitance measured using the high frequency voltage. As a result, the measureable time can be ensured to be long, and together with shortening of the particulate collection time due to using the above-mentioned low frequency voltage, the PM concentration can be detected over a longer time. In addition, the number of times repeating steps of particulate collection, measurement, and regeneration can be reduced, with the aim of further reducing the power consumption.

In the present embodiment, the means related to execution of Step S22 of FIG. 9 constitute a voltage application start means, the means related to execution of Steps S23 constitute a first measurement means, the means related to execution of Steps S24 and S25 constitute a voltage application stop means, the means related to execution of Step S26 constitute a second measurement means, and the means related to execution of Step S27 constitute a concentration detection means.

Third Embodiment

The PM sensor 31 related to the third embodiment is one in which a portion of the configuration of the sensor element 12 of the PM sensor 11 related to the first embodiment and the constitution of the ECU 16 has been changed.

FIG. 12 is an exploded perspective view of the sensor element 32 of the PM sensor 31 related to the third embodiment.

As shown in FIG. 12, the configuration of the sensor element 32 is similar to the configuration of the PM sensor 11 related to the first embodiment except for being without a measurement electrode layer. In the present embodiment, without providing measurement electrodes as in the first embodiment, the electrode units 323A and 327A function as both particulate collection electrodes and measurement electrodes, and the impedance measuring instrument 14 is electrically connected to the electrode plates 330 and 331 via a change-over switch.

The change-over switch operates based on a control signal sent from the ECU 36, and selectively changes a connection to the electrode plates 330 and 331 between the DC power source 13 for particulate collection and the impedance measuring instrument 14.

More specifically, in a case of applying particulate collection voltage to the electrode units 323A and 327A, the DC power source 13 for particulate collection and the electrode plates 330 and 331 are connected, and in a case of measuring the capacitance of the sensor element 32, the impedance measuring instrument 14 and the electrode plates 330 and 331 are connected.

FIG. 13 is a view schematically illustrating an aspect when PM is collected inside of the particulate collection portion 320 of the sensor element 32 of the present embodiment. As shown in FIG. 13, PM being collected deposits to an inner wall inside the particulate collection portion 320. At this time, the capacitance of the particulate collection portion 320 is influenced by the PM thus deposited, and thus changes. From this change in capacitance being correlated to the PM deposition amount, it becomes possible to detect PM based on the change in this capacitance.

In addition, similarly to the first embodiment, the capacitance of the sensor element 32 is obtained by measuring the capacitance of the particulate collection portion 320 also in the present embodiment. That is, in the following explanation, the capacitance of the particulate collection portion 320 indicates the capacitance of the sensor element 32.

Figure 14:
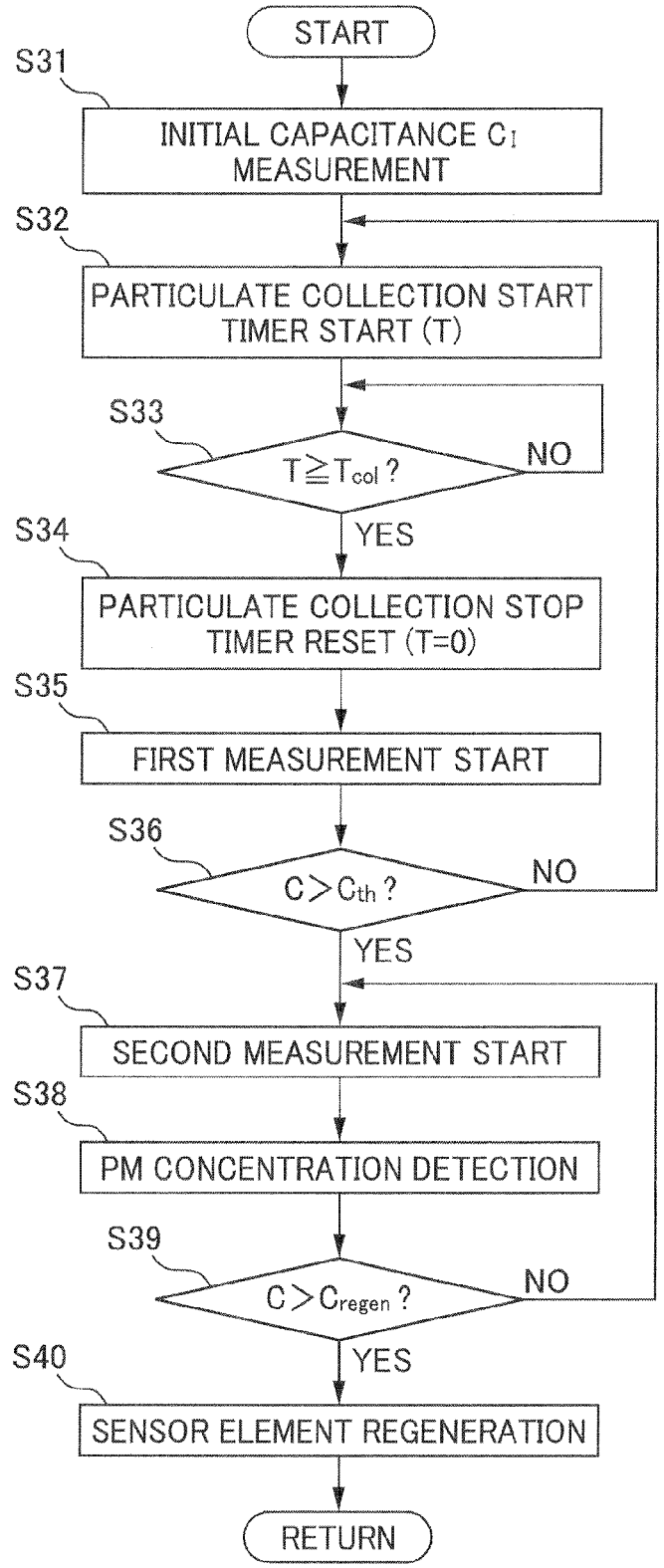
FIG. 14 is a flowchart showing steps of PM concentration detection using a PM sensor 31.

FIG. 14 is a flowchart showing steps of detecting PM concentration in exhaust using the PM sensor 31. This flowchart is repeatedly carried out by the ECU 36 after engine start-up.

In Step S31, the capacitance of the particulate collection portion 320 is measured, and this is stored as the initial capacitance $C_I$.

In Step S32, particulate collection voltage is applied to the particulate collection electrodes 323A and 327A, and a timer is started, thereby starting particulate collection over a predetermined time. More specifically, the DC power source for particulate collection is connected to the electrode units 323A and 327A, thereby applying particulate collection voltage thereto. As a result, PM contained in the exhaust is caused to adhere to the particulate collection portion 320.

In Step S33, it is determined whether at least a predetermined time $T_{col}$ set in advance has elapsed since starting particulate collection. In a case of the determination being YES, the procedure advances to Step S34, and in a case of being NO, particulate collection is continued. It should be noted that the predetermined time $T_{col}$ is set to a predetermined value from carrying out experiments and the like beforehand.

In Step S34, the application of particulate collection voltage to the electrode units 323A and 327A is stopped, thereby stopping particulate collection, and the timer is reset. As a result, the collection of PM due to the application of particulate collection voltage is stopped.

In Step S35, a first measurement is started. More specifically, measurement voltage is applied to the electrode units 323A and 327A, and the capacitance of the particulate collection portion 320 is measured. During measurement, the impedance measuring instrument is connected to the electrode units 323A and 327A, and measurement voltage is applied thereto.

In Step S36, it is determined whether a capacitance C measured in the first measurement of Step S35 exceeds a predetermined threshold value $C_{th}$ set in advance. In a case of the determination being YES, the procedure advances to Step S37, and in a case of being NO, the procedure returns to Step S32 and starts particulate collection again.

In Step S37, a second measurement is started. More specifically, measurement voltage is applied to the electrode units 323A and 327A, and the capacitance of the particulate collection portion 320 is measured.

In Step S38, the PM concentration in the exhaust is detected.

More specifically, a value is calculated that is the initial capacitance $C_I$ measured in Step S31 subtracted from the capacitance measured in the second measurement of Step S37, and this value is stored as the variation amount of capacitance $\Delta C$ (i.e. the variation amount of capacitance of the particulate collection portion before and after particulate collection).

Next, PM concentration in the exhaust is detected according to the variation amount of capacitance ΔC. More specifically, the PM concentration according to the variation amount of capacitance ΔC thus measured is calculated based on a control map that correlates variation amount of capacitance ΔC of the particulate collection portion and PM concentration in the exhaust. It should be noted that the control map is prepared by performing predetermined experiments beforehand, and is stored in the ECU 36.

In Step S39, it is determined whether the capacitance measured in the second measurement of Step S37 exceeds a regeneration determination value $C_{regen}$ of the sensor element 32. Here, the regeneration determination value $C_{regen}$ is a value that is slightly smaller than a maximum measureable capacitance $C_{max}$ of the sensor element 32, and is preferably a value 0.95 times the maximum capacitance $C_{max}$.

In a case of the determination being YES, the procedure advances to Step S40, and in a case of being NO, the procedure returns to Step S37 and starts the second measurement again. It should be noted that, at this time, the sensor element 32 can start the second measurement due to being in a state in which a change in capacitance of the particulate collection portion 320 is apparent.

In Step S40, regeneration of the sensor element 32 is carried out. More specifically, the particulate collection portion 320 is heated by passing a predetermined current to the heater layer to cause heat generation, and PM adhered to the particulate collection portion 320 is combustively removed.

According to the present embodiment, except for providing two electrode units, similar effects to the first embodiment are achieved.

In addition, in the present embodiment, the means related to execution of Steps S32 to S34 of FIG. 14 constitute a voltage application means, the means related to execution of Step S35 constitute a first measurement means, the means related to execution of Step S36 constitute a determination means, the means related to execution of Step S37 constitute a second measurement means, and the means related to execution of Step S38 constitute a concentration detection means.

Fourth Embodiment

The PM sensor 41 related to the fourth embodiment is a similar configuration to the third embodiment except for the configuration of the ECU 36 of the PM sensor 31 related to the third embodiment, more specifically portions constituting the first measurement means and the second measurement means being different.

In addition, similarly to the first embodiment, the electrical characteristic of the sensor element is obtained by measuring the electrical characteristic of the particulate collection portion also in the present embodiment. That is, in the following explanation, the capacitance of the particulate collection portion indicates the capacitance of the sensor element.

Figure 15:
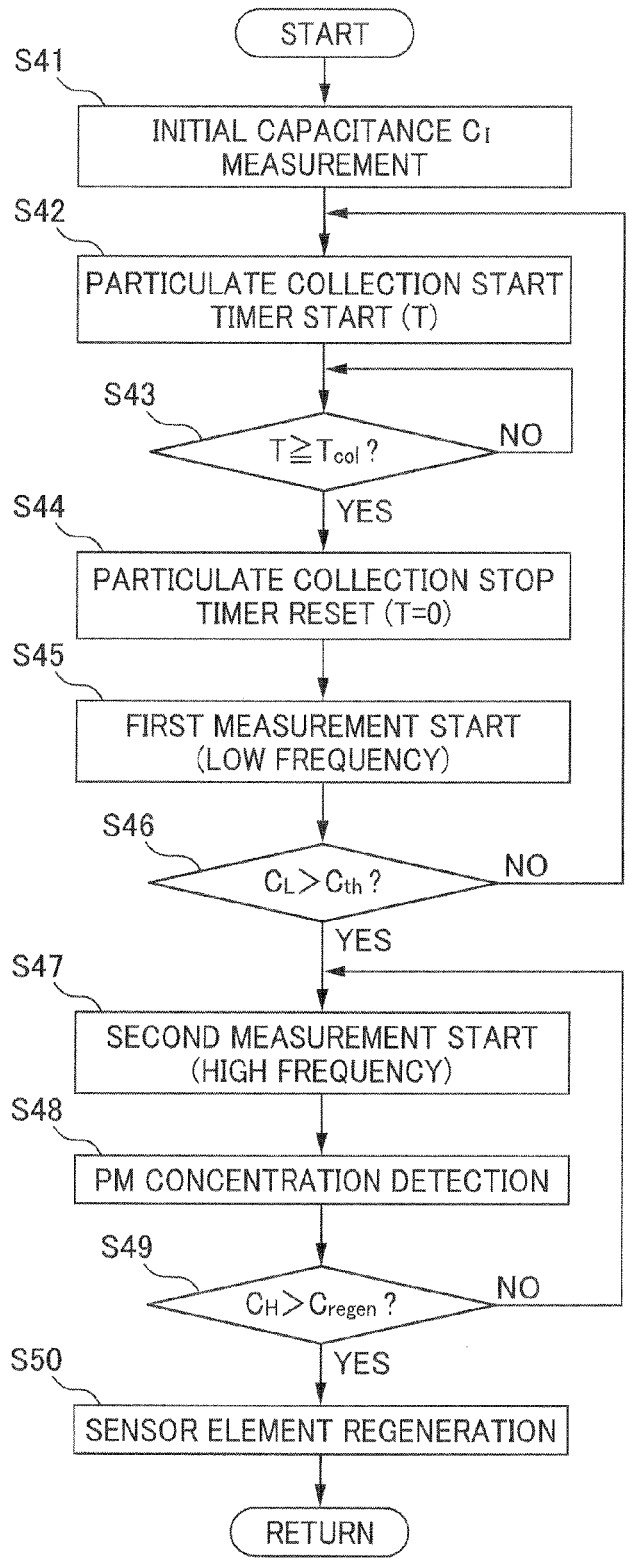
FIG. 15 is a flowchart showing steps of PM concentration detection using a PM sensor 41.

FIG. 15 is a flowchart showing steps of detecting PM concentration in exhaust using the PM sensor 41. This flowchart is repeatedly carried out by the ECU 46 after engine start-up.

In Step S41, the capacitance of the particulate collection portion is measured, and this is stored as an initial capacitance $C_I$.

In Step S42, particulate collection voltage is applied to the electrode units, and a timer is started, thereby starting particulate collection over a predetermined time. More specifically, the DC power source for particulate collection is connected to the electrode plates having electrode units, thereby applying particulate collection voltage thereto. As a result, PM contained in the exhaust is caused to adhere to the particulate collection portion.

In Step S43, it is determined whether at least a predetermined time $T_{col}$ set in advance has elapsed since starting particulate collection. In a case of the determination being YES, the procedure advances to Step S44, and in a case of being NO, particulate collection is continued. It should be noted that the predetermined time $T_{col}$ is set to a predetermined value from carrying out experiments and the like beforehand.

In Step S44, the application of particulate collection voltage to the electrode units is stopped, thereby stopping particulate collection, and the timer is reset. As a result, the collection of PM due to the application of particulate collection voltage is stopped.

In Step S45, a first measurement is started. More specifically, measurement voltage, of a frequency that is lower than a frequency of the measurement voltage applied in the second measurement described above, is applied to the electrode units, and a capacitance $C_L$ of the particulate collection portion is measured. During measurement, the impedance measuring instrument is connected to the electrode units, and measurement voltage is applied thereto.

In Step S46, it is determined whether a capacitance $C_L$ measured in the first measurement of Step S45 exceeds a predetermined threshold value $C_{th}$ set in advance. In a case of the determination being YES, the procedure advances to Step S47, and in a case of being NO, the procedure returns to Step S42 and starts particulate collection again.

In Step S47, a second measurement is started. More specifically, measurement voltage, of a frequency that is higher than a frequency of the measurement voltage applied in the first measurement described above, is applied to the electrode units, and a capacitance $C_H$ of the particulate collection portion is measured.

In Step S48, the PM concentration in the exhaust is detected.

More specifically, a value is calculated that is the initial capacitance $C_I$ measured in Step S41 subtracted from the capacitance $C_H$ measured in the second measurement of Step S47, and this value is stored as the variation amount of capacitance ΔC (i.e. the variation amount of capacitance of the particulate collection portion before and after particulate collection).

Next, the PM concentration in exhaust is detected according to the variation amount of capacitance ΔC. More specifically, the PM concentration according to the variation amount of capacitance ΔC thus measured is calculated based on a control map that correlates the variation amount of capacitance ΔC of the particulate collection portion and PM concentration in exhaust. It should be noted that the control map is prepared by performing predetermined experiments beforehand, and is stored in the ECU 46.

In Step S49, it is determined whether the capacitance $C_H$ measured in the second measurement of Step S47 exceeds a regeneration determination value $C_{regen}$ of the sensor element. Here, the regeneration determination value $C_{regen}$ is a value that is slightly smaller than a maximum measureable capacitance $C_{max}$ of the sensor element, and is preferably a value by multiplying 0.95 times the maximum capacitance $C_{max}$.

In a case of the determination being YES, the procedure advances to Step S50, and in a case of being NO, the procedure returns to Step S47 to start the second measurement again. It should be noted that, at this time, the sensor element can start the second measurement due to being in a state in which a change in capacitance of the particulate collection portion is apparent.

In Step S50, regeneration of the sensor element is carried out. More specifically, the particulate collection portion is heated by passing a predetermined current to the heater layer to cause heat generation, and PM adhered to the particulate collection portion is combustively removed.

According to the present embodiment, except for providing two electrode units, similar effects to the second embodiment are achieved.

In addition, in the present embodiment, the means related to execution of Steps S42 to S44 of FIG. 15 constitute a voltage application means, the means related to execution of Step S45 constitute a first measurement means, the means related to execution of Step S46 constitute a determination means, the means related to execution of Step S47 constitutes a second measurement means, and the means related to execution of Step S48 constitute a concentration detection means.

It should be noted that the present embodiments are not limited to the embodiments described above, and various modifications thereto are possible.

For example, in the first to fourth embodiments described above, determination of particulate collection stopping or determination of second measurement starting was performed according to whether a capacitance C measured by the first measurement exceeded a predetermined threshold value $C_{th}$; however, these determinations may be performed according to whether a predetermined time period has elapsed. In addition, seeking a linear slope from the curve representing a relationship between capacitance C and time when the capacitance beings to change, these determinations may be made according to this slope.

In addition, a configuration may be made, for example, so that a transient operation state determination unit is provided in the ECU of the first to fourth embodiments described above as a means related to execution of Steps S12, S22, S32, and S42, and, in a case of the engine being in a transient operation state being determined by the transient operation state determination portion, particulate collection is started by applying voltage to the particulate collection electrodes.

As a result, in a transient operation state in which more PM is emitted, a state in which PM adheres entirely over the particulate collection portion and a change in the electrical characteristic of the particulate collection portion is apparent is brought about efficiently in a short time period, and the PM concentration in exhaust gas can be detected. It should be noted that the determination of whether it is a transient operation state is determined based on a fuel injection amount calculated by the ECU based on a throttle angle detected by an accelerator sensor that detects a depressed amount of the accelerator pedal of a vehicle propelled by an engine, or the output of the accelerator sensor.

What is claimed is:

1. A particulate matter detection device provided in an exhaust path of an internal combustion engine, including a sensor element to which particulate matter contained in exhaust adheres, and detecting a concentration of particulate matter in exhaust based on an electrical characteristic of the sensor element, wherein the sensor element includes a first electrode unit to which a particulate collection voltage for causing particulate matter contained in exhaust to adhere to the sensor element is applied, and a second electrode unit to which a measurement voltage for measuring an electrical characteristic of the sensor element is applied, and wherein the particulate matter detection device comprises:
  a voltage application start means for starting application of particulate collection voltage to the first electrode unit;
  a first measurement means for measuring the electrical characteristic of the sensor element by applying measurement voltage to the second electrode unit, after the application of the particulate collection voltage has started;
  a voltage application stop means for stopping application of particulate collection voltage to the first electrode unit in response to a predetermined condition being satisfied;
  a second measurement means for measuring the electrical characteristic of the sensor element by applying measurement voltage to the second electrode unit, after stopping application of the particulate collection voltage; and
  a concentration detection means for detecting a concentration of particulate matter in the exhaust based on a measurement value of the second measurement means.

2. The particulate matter detection device according to claim 1, wherein:
  the first measurement means and the second measurement means are means for applying a measurement voltage of an alternating current to the second electrode unit, and
  when a frequency of a measurement voltage applied to the second electrode unit by the first measurement means is set as a first frequency, and a frequency of a measurement voltage applied to the second electrode unit by the second measurement means is set as a second frequency, the second frequency is higher than the first frequency.

3. The particulate matter detection device according to claim 1, further comprising a transient operation state determination means for determining whether an operation state of the internal combustion engine is a transient operation state,
  wherein the concentration detection means starts application of the particulate collection voltage by the voltage application start means in a case where the transient operation state determination means determines a transient operation state.

4. The particulate matter detection device according to claim 1, wherein the particulate collection voltage is large compared to the measurement voltage.

5. The particulate matter detection device according to claim 1, wherein the predetermined condition is whether a value calculated based on the measurement value of the first measurement means exceeds a predetermined threshold value.

* * * * *